US00PP08182P

United States Patent [19]

Saville

[11] Patent Number: Plant 8,182

[45] Date of Patent: Mar. 23, 1993

[54] MINIATURE ROSE PLANT NAMED SAVAFIRE

[75] Inventor: F. Harmon Saville, Rowley, Mass.

[73] Assignee: Nor'East Miniature Roses, Inc., Rowley, Mass.

[21] Appl. No.: 746,232

[22] Filed: Aug. 15, 1991

[51] Int. Cl.[5] ..... A01H 5/00

[52] U.S. Cl. ..... Plt./7.1

[58] Field of Search ..... Plt./2, 7.1

[56] References Cited

U.S. PATENT DOCUMENTS

P. 5,274 8/1984 Bennet ..... Plt. 7.1

*Primary Examiner*—Howard J. Locker

*Attorney, Agent, or Firm*—Christie, Parker & Hale

[57] ABSTRACT

A new miniature rose with red and yellow bi-colored flowers of good form.

1 Drawing Sheet

SUMMARY OF THE INVENTION

The present invention relates to a new and distinct variety of rose plant of the miniature rose class, which was created by me by crossing as seed parent an unnamed, unpatented seedling of my creation and as pollen parent the rose known as "Rainbow's End" (U.S. Plant Pat. No. 5,482). The varietal denomination of this new rose is "Savafire".

Among the novel characteristics possessed by this new variety which distinguishes it from its parent and all other varieties of which I am aware is its attractive red and yellow bi-color flowers of good form which open well.

Asexual reproduction by propagation by cuttings of the new variety as performed in Essex County, Mass. shows that the foregoing and other distinguishing characteristics come true to form and are established and transmitted through succeeding propagations.

BRIEF DESCRIPTION OF ILLUSTRATION

The accompanying illustration shows typical specimens of the flowers of the new variety in different stages of development depicted in color as nearly true as it is reasonably possible to make the same in a color illustration of this character.

DETAILED DESCRIPTION OF THE NEW VARIETY

The following is a detailed description of my new variety, with color terminology in accordance with The Royal Horticultural Society Colour Chart (R.H.S.C.C.). The terminology used in color description herein refers to plate numbers in the aforementioned color chart.

Parentage:

*Seed parent.*—Unnamed seedling.

*Pollen parent.*—"Rainbow's End".

Class: Miniature.

The following observations are made of specimens grown under glass in Essex County, Mass., during the month of July.

Flower

Blooming habit: Continuous.

A. Bud:

(1) *Size.*—Medium.

(2) *Form.*—Pointed, ovoid.

(3) *Color.*—As sepals divide, bud color is near 7A edged with near 40A to 41A.

(4) *Sepals.*—Foliated, longer than bud.

(5) *Peduncle.*—Length — about 182 -inches. Aspect — straight. Strength — erect. Color — light green with purplish tones.

B. Bloom:

(1) *Size.*—Average size when fully expanded — about 1½ inches.

(2) *Borne.*—Singly, one to a stem and several together in sprays of 3 to 20 blooms.

(3) *Form.*—High centered at first becoming flat; outer petals quill to points and roll under; outer petals tend to have pointed apices.

(4) *Petalage.*—Number of petals under normal conditions — about 35.

(5) *Color.*—After sepals fall and petals unfurl, predominant flower color of visible petal undersurface is near 12B-D to 14C-D flushed with near 41A. Petal top surfaces have near 41A to 42A edges with red coloration washing into yellow coloration of the petal top surface toward flower center. Red colored washing tends to extend deeper on outer petals and becomes more extensive as blooms open and age. Red and yellow bi-color effect is more distinct through the ⅓ to ½ open stage; red color appearance is more dominant in open blooms. General tonality from a distance is a bright orange red/yellow bi-color. Color at point of petal attachment is near 12A.

C. Petals:

(1) *Texture.*—Average.

(2) *Appearance.*—Inside velvety and outside satiny.

(3) *Form.*—Fan shaped; some curved pointed apices.

(4) *Arrangement.*—Regularly arranged, imbricated.

(5) *Petaloids in center.*—Few.

(6) *Persistence.*—Average.

(7) *Fragrance.*—Slight.

(8) *Lasting quality.*—Long lasting quality on plant and after cutting.

Reproductive Organs

A. Stamens, filaments and anthers:

*Arrangement and color.*—Regularly arranged around styles. Color — near 21C.

B. Pollen:
*Color.*—Near 17C.
C. Styles: Thin, medium length.
D. Stigmas:
*Color.*—Near 156B.
E. Hips: None observed.

Plant

A. Form: Compact.
B. Growth: Very vigorous, uniform branching.
*Height attained.*—About 15 to 18 inches.
C. Foliage: Compound 5 to 7 leaflets.
(1) *Size.*—Medium.
(2) *Quantity.*—Abundant.
(3) *Color.*—New foliage: Upper side — near 137B. Under side — near 148B. Old foliage: Upper side — near 137A. Under side — near 147C.
(4) *Shape.*—Oval, pointed.
(5) *Texture.*—Upper side is semi-glossy; under side is matte.
(6) *Edge.*—Serrate.
(7) *Serration.*—Regular.

(8) *Leaf stem.*—Color — near 146A. Under side — 141C.
(9) *Stipules.*—Medium length, slightly bearded.
(10) *Resistance to disease.*—Blackspot — Average. Mildew — Average. Rust — Average.
D. Wood:
(1) *New wood.*—Color — near 183D. Bark — smooth.
(2) *Old wood.*—Color — near 137C. Bark — smooth.
E. Thorns:
(1) *Thorns.*—Quantity (main stalk) — ordinary. On laterals from stalk — few. Form — long, thin, curved downward. Length — medium. Color — near 185B. Position — irregular.
(2) Prickles.—None.
F. Winter hardiness: Needs protection in severe climates.

I claim:

1. A new and distinct variety of rose plant of the miniature rose class, substantially as shown and described.

* * * * *

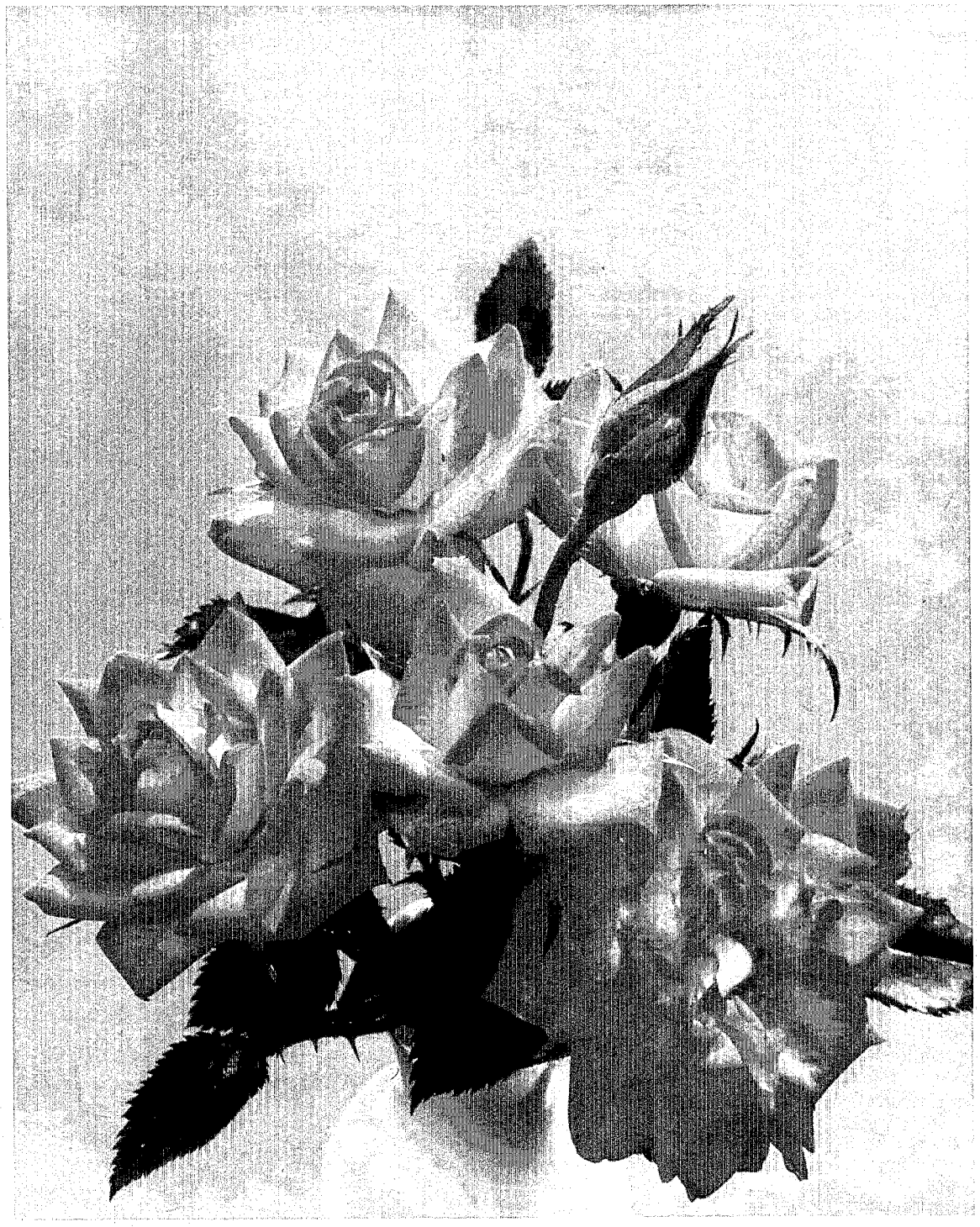

UNITED STATES PATENT AND TRADEMARK OFFICE

CERTIFICATE OF CORRECTION

PATENT NO. : Plant 8,182

DATED : March 23, 1993

INVENTOR(S) : F. Harmon Saville

It is certified that error appears in the above-identified patent and that said Letters Patent is hereby corrected as shown below:

Column 2, line 6, change "182 -inches" to -- 3/4 -inch --.

Signed and Sealed this

Twenty-first Day of June, 1994

Bruce Lehman

*Attest:*

BRUCE LEHMAN

*Attesting Officer*

*Commissioner of Patents and Trademarks*